United States Patent [19]

Lang

[11] 4,025,301
[45] May 24, 1977

[54] AZO DYES DERIVED FROM 3-AMINO PYRIDINE IN HAIR DYE COMPOSITIONS

[75] Inventor: Gerard Lang, Epinay-sur-Seine, France

[73] Assignee: Societe Anonyme dite: L'Oreal, Paris, France

[22] Filed: Sept. 26, 1975

[21] Appl. No.: 617,159

[30] Foreign Application Priority Data

Sept. 27, 1974 Luxembourg ............................ 015

[52] U.S. Cl. ......................................... 8/10.1; 8/10; 8/11; 8/32; 8/41 R; 260/156; 424/DIG. 1; 424/DIG. 2; 424/71
[51] Int. Cl.² .......................................... A61K 7/13
[58] Field of Search ............ 260/156; 8/10.1, 10.2, 8/10, 11, 32, 41 R; 132/7

[56] References Cited

UNITED STATES PATENTS

| 2,864,813 | 12/1958 | Bossard et al. ..................... 260/156 |
|---|---|---|
| 2,893,816 | 7/1959 | Tsang et al. ....................... 260/156 |
| 3,051,697 | 8/1962 | Lewis et al. ....................... 260/156 |
| 3,117,116 | 1/1964 | Randvere ........................... 260/156 |
| 3,118,871 | 1/1964 | Brody et al. ....................... 260/156 |
| 3,249,597 | 5/1966 | Dehn et al. ........................ 260/156 |
| 3,312,681 | 4/1967 | Lewis .............................. 260/156 |
| 3,393,190 | 7/1968 | Stright ............................ 260/156 |

Primary Examiner—Sam Rosen
Assistant Examiner—Vera C. Clarke
Attorney, Agent, or Firm—Cushman, Darby & Cushman

[57] ABSTRACT

A composition for dyeing hair comprises in a cosmetic vehicle at least one dye compound of the formula

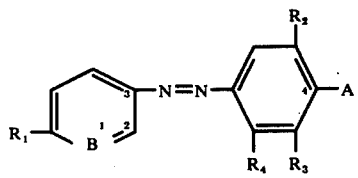

wherein B is selected from the group consisting of

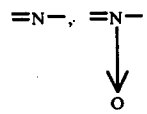

and

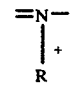

wherein R is lower alkyl containing 1–4 carbon atoms, $R_1$ is selected from the group consisting of hydrogen, lower alkyl containing 1-4 carbon atoms, lower alkoxy containing 1-4 carbon atoms and chlorine, $R_2$ is selected from the group consisting of hydrogen, methyl and methoxy, $R_4$ is selected from the group consisting of hydrogen, methyl, chlorine, nitro, amino and acetylamino, $R_3$ is hydrogen or together with $R_4$ forms an unsaturated 6 membered ring carrying a hydroxy substituent chelated with one of the nitrogen atoms of the azo link, and

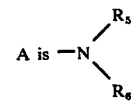

where $R_5$ is selected from the group consisting of hydrogen, -$CH_3$, -$C_2H_5$ and β-hydroxyethyl, and $R_6$ is selected from the group consisting of hydrogen, —$CH_3$, —$C_2H_5$, β-hydroxyethyl, phenyl and -$CH_2SO_3Na$, with the proviso that when B is

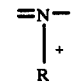

the anion X⁻ associated with the quaternized nitrogen atom is the anion residue of a member selected from the group consisting of organic acid and mineral acid, said composition having a pH ranging from 3 to 11 and said compound being present in an amount ranging from 0.001 to 1 percent by weight of said composition.

17 Claims, No Drawings

AZO DYES DERIVED FROM 3-AMINO PYRIDINE IN HAIR DYE COMPOSITIONS

The present invention relates to dye compositions for living human hair containing azo dyes derived from 3-amino pyridine.

More particularly, the present invention relates to a dye composition for human hair containing in solution one or more compounds of the formula

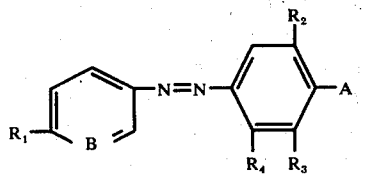

wherein B is selected from the group consisting of $=N-$,

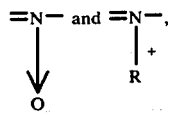

R is lower alkyl containing 1–4 carbon atoms, $R_1$ is selected from the group consisting of hydrogen, lower alkyl containing 1–4 carbon atoms, lower alkoxy containing 1–4 carbon atoms and chlorine, $R_2$ is selected from the group consisting of hydrogen, methyl and methoxy, $R_4$ is selected from the group consisting of hydrogen, methyl, chlorine, nitro, amino and acetylamino, $R_3$ is hydrogen or together with $R_4$ form an unsaturated 6 membered ring carrying a hydroxy substituent chelated with one of the nitrogen atoms of the azo link, and

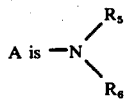

wherein $R_5$ is selected from the group consisting of hydrogen, methyl, ethyl and β-hydroxyethyl and $R_6$ is selected from the group consisting of hydrogen, methyl, ethyl, β-hydroxyethyl, phenyl or $-CH_2-SO_3Na$, with the proviso that when B is

the anion $X^-$ associated with the quaternized nitrogen atom is derived from an organic or mineral acid, this anion being for example methosulfate, ethosulfate, bromide, iodide or chloride.

The dyes of formula (I) provide stable and luminous shades ranging from yellows to blues and exhibit a range more extensive in the yellows than the azo dyes derived from previously known 2-amino pyridine.

The dyes of the present invention exhibit good solubility in cosmetic solvents, good affinity for keratinic fibers and they exhibit in general excellent stability in solution which is a highly desired characteristic of cosmetic solutions and lotions, and principally hair dye compositions.

The hair dye compositions of the present invention comprise an aqueous or hydro-alcoholic solution prepared by dissolving in water or in a water-alcohol mixture, one or more compounds of formula I, or even by solutions in such solvents as propylene glycol or butyl cellosolve, i.e. ethylene glycol monobutyl ether. The alcohols employed in the compositions of the present invention are generally ethanol or isopropanol present in amounts of about 5 to 70 weight percent, whereas the said solvents are employed in amounts of 5 to 15 weight percent, of said composition.

The concentration of the compounds of formula I in the hair dye compositions of this invention can vary to a large degree because of their good affinity for hair. Generally the compounds of formula I are present in an amount between 0.001 and 1 percent by weight relative to the total weight of the composition.

The pH of the hair dye composition of this invention can also vary to a large degree and generally the pH ranges from 3 to 11. The pH of the composition can be adjusted to the desired value by the addition of a cosmetically acceptable acid or base, such as orthophosphoric acid, citric acid, monoethanolamine, triethanolamine and ammonia.

The compositions of the present invention can also contain various adjuvants conventionally employed in hair dye compositions such as wetting agents, dispersing agents, swelling agents, penetrating agents, emollients and perfumes. Advantageously, the hair dye compositions of the present invention are packaged under pressure in aerosol containers together with an aerosol propellant.

The hair dye compositions of the present invention can also include other direct hair dyes such as azo or anthraquinone dyes, nitrobenzene dyes, indoanilines, indophenols or indamines.

The compositions of the present invention can be employed to impart a durable coloration to hair in which case the composition is applied to the hair for a period ranging from about 3 to 40 minutes, after which the hair is rinsed, washed and dried.

The compositions of the present invention can also be employed as lotions or rinses to impart to the hair a light coloration. When so employed they are applied to previously washed hair and the hair is not rinsed after application of the composition thereto.

Also the compositions of this invention can be used in the form of hair setting lotions which not only impart to the hair a light coloration but also improve the hold of the hair. In this case, the compositions are provided in the form of a hydroalcoholic solution which includes at least one cosmetic resin. These hair setting lotions are applied to previously washed and rinsed moist hair which is then put up on rollers and dried.

Representative cosmetic resins usefully employed in the hair setting lotions of this invention include polyvinylpyrrolidone having a molecular weight ranging from 10,000 to 700,000, copolymers of crotonic acid and vinyl acetate having a molecular weight of about 40,000 to 200,000 wherein the ratio of VA/CA is preferably about 90/10, copolymers of vinylpyrrolidone and vinyl acetate having a molecular weight ranging between about 40,000 and 160,000 wherein the ratio of VP to VA ranges between 30/70 and 70/30, copolymers of maleic anhydride and butylvinyl ether and copolymers of maleic anhydride and methyl vinyl ether and their ethyl, isopropyl and butyl esters. The cosmetic resin is employed in amounts of 1–3 percent by weight of said composition.

The hair setting lotions of the present invention generally include 20 to 70 weight percent of a low molecular weight alcohol, preferably ethanol or isopropanol.

The present invention also relates to the compounds of formula I among which when B is =N—, in the prefered compounds $R_1$ is different from H and one $R_4$, $R_5$ or $R_6$ are not alkyl or —$C_6H_5$ when $R_1$ is H.

Compounds of formula I wherein B is =N— and

are prepared in accordance with a known process by the diazotization of a corresponding 3-amino pyridine or 3-amino pyridine N-oxide, and coupling the resulting diazonium salt with a compound of the formula

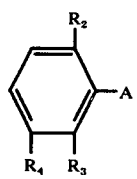

wherein $R_2$, $R_3$, $R_4$ and A have the meanings given above.

Compounds of formula I wherein B is

are prepared by reacting an alkylating agent RX wherein X has the meaning given above on the said compound wherein B is =N—.

The compositions of the present invention can also contain $H_2O_2$ and thus be employed as hair lightening compositions. The compositions of the present invention can also be employed together with an oxidation dye and an oxidizing agent such as $H_2O_2$ which can be added at the moment of use.

Preferably $H_2O_2$ (200 volumes) is employed but it is to be understood that $H_2O_2$ of other strengths such as 20, 30 or 100 volumes can also be employed.

The range of the pH is adjusted to between 3 to 7 when the compositions contain quaternary compounds of formula I which are not stable in a basic medium.

The colorations obtained with the compositions of the present invention are often distinguished by their excellent stability to light and weathering and by their good holding to washing.

The following non-limiting examples illustrate the present invention. Unless otherwise indicated, all parts and percentages are by weight and all degress are in centigrade.

Examples of Preparation

EXAMPLE 1

Preparation of 4'-dimethylamino benzene -1':3 azo pyridine of the formula

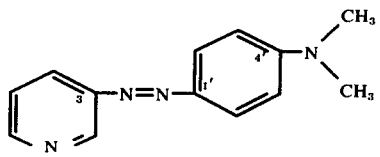

0.1 mole of 3-amino pyridine is dissolved in 50cm³ of 5N HCl. The solution is cooled to +5° C and there are added, dropwise, 13.3cm³ of an aqueous 7.5N solution of sodium nitrite. The resulting mixture is agitated for 15 minutes at +5° C. To the solution thus obtained there is added 0.1 mole of N,N-dimethyl aniline in 12cm³ of acetic acid. The resulting mixture is stirred for 30 minutes. The above dye is then precipitated by the addition of 40g of crystallized sodium acetate. The reaction mixture is then filtered to recover the precipitate which is then washed with water and dried. The product, recrystallized in cyclohexane has a melting point of 122° C.

Analysis: $C_{13}H_{14}N_4$

|  | %C | %H | %N |
| --- | --- | --- | --- |
| Calculated | 69.00 | 6.20 | 24.80 |
| Found | 68.83 | 6.13 | 24.72 |

EXAMPLE 2

Preparation of 4'-N, N-bis (2-hydroxyethyl) amino benzene -1':3 azo pyridine of the formula

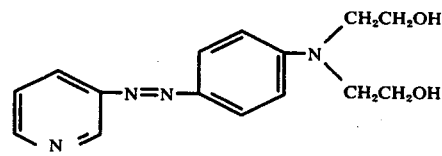

There is slowly added, with agitation and while maintaining the temperature at 5° C, a solution of 0.1 mole of the diazonium salt prepared in Example 1 to a solution of 0.1 mole of N,N-bis (2-hyrroxyethyl) aniline in 18cm₃ of acetic acid. The resulting mixture is agitated for 30 minutes and the above dye is then precipitated by the addition thereto of 40g of crystallized sodium acetate. The precipitate is filtered, washed with water and dried. The product, recrystallized in 50% isopropanol melts at 126° C.

Analysis: $C_{15}H_{18}N_4O_2$

|  | %C | %H | %N |
| --- | --- | --- | --- |
| Calculated | 62.95 | 6.29 | 19.58 |
| Theory | 62.72 | 6.40 | 19.61 |

EXAMPLE 3

Preparation of the sodium salt of pyridine -3':4 azo anilino methyl sulfonic acid of the formula

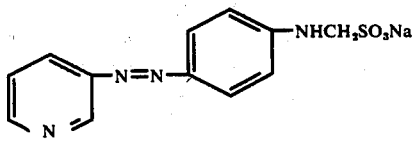

There is slowly added, with agitation and while maintaining the temperature at 5° C, a solution of 0.1 mole of the diazonium salt prepared in Example 1 to a solution of 0.11 mole of the ω-salt of aniline in 180cm³ of water containing 60g of crystallized sodium acetate. The resulting mixture is agitated for 15 minutes at which time there are added 300g of crystallized sodium acetate. The mixture is again agitated for 15 minutes and then filtered to recover the above dye which when recrystallized in water exhibits a melting point above 300° C.

Analysis: $C_{12}H_{11}N_4O_3SNa \cdot 0.5H_2O$

|  | %C | %H | %N |
|---|---|---|---|
| Calculated | 44.60 | 3.72 | 17.35 |
| Found | 44.42 | 4.30 | 17.43 |

EXAMPLE 4

Preparation of 4'-amino-8'-hydroxy naphthalene-1':3 azo pyridine having the formula

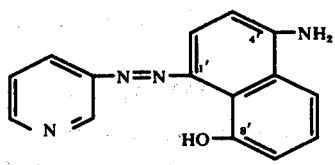

There is slowly added, with agitation and while maintaining the temperature at 5° C, a solution of 0.1 mole of the diazonium salt prepared in Example 1 to a solution of 0.1 mole of 5-hydroxy naphthylamine-1 in 400cm³ of 50% ethyl alcohol and 80cm³ of acetic acid. The resulting mixture is agitated for 30 minutes at which time there are added 80g of crystallized sodium acetate. The reaction mixture is filtered to recover the above dye which is then washed with water and dried. The product melts at 250° C with decomposition.

Analysis: $C_{15}H_{12}N_4O \cdot 0.25H_2O$

|  | %C | %H | %N |
|---|---|---|---|
| Calculated | 67.10 | 4.66 | 20.81 |
| Found | 67.30 | 4.72 | 20.76 |

EXAMPLE 5

Preparation of 4'-dimethylamino-2'-nitro benzene-1':3 pyridine having the formula

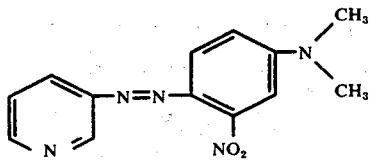

There is slowly added, with agitation and while maintaining the temperature at 5° C, a solution of 0.1 mole of the diazonium salt prepared in Example 1 to a solution of 0.1 mole of N,N-dimethyl metanitraniline in 50cm³ of acetic acid. The resulting mixture is agitated for 30 minutes and then filtered to recover the above precipitated dye which is then washed with water and recrystallized in ethyl alcohol. The product melts at 156° C.

Analysis: $C_{13}H_{13}N_5O_2$

|  | %C | %H | %N |
|---|---|---|---|
| Calculated | 57.60 | 4.80 | 25.80 |
| Found | 57.92 | 5.05 | 25.86 |

EXAMPLE 6

Preparation of 4'-phenylamino benzene-1':3 azo pyridine having the formula

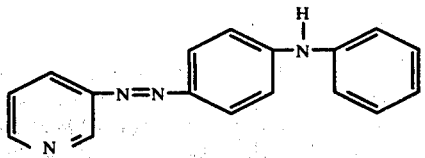

There is slowly added, with agitation and while maintaining the temperature at 5° C, a solution of 0.1 mole of the diazonium salt prepared in Example 1 to a solution of 0.1 mole of diphenylamine in 121cm³ of 90% ethyl alcohol and 6cm³ of concentrated HCl. The resulting mixture is agitated for 1 hour at which time there are added thereto 80g of crystallized sodium acetate. The reaction mixture is then filtered to recover the precipitated dye which is then washed with water and dried. It has a melting point of 204° C.

Analysis: $C_{17}H_{14}N_4 \cdot H_2O$

|  | %C | %H | %N |
|---|---|---|---|
| Calculated | 69.90 | 5.48 | 19.20 |
| Found | 70.29 | 5.58 | 19.12 |

EXAMPLE 7

Preparation of 4'-dimethylamino benzene-1':3 azo 6-methyl pyridine having the formula

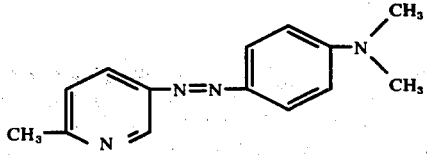

0.1 mole of 3-amino-6-methyl pyridine is dissolved in 50cm³ of 5N HCl. The solution is cooled to +5° C and there are added thereto, dropwise, 13.3cm³ of an aqueous 7.5N solution of sodium nitrite. The resulting mixture is agitated for 15 minutes at +5° C. To the resulting solution there is added 0.1 mole of N,N-dimethylaniline in 12cm³ of acetic acid. This mixture is then agitated for 30 minutes at which time the above dye is precipitated by the addition thereto of 40g of crystallized sodium acetate. The dye precipitate is filtered, washed with water and dried. When recrystallized in ethyl alcohol it melts at 153° C.

Analysis: $C_{14}H_{16}N_4$

|  | %C | %H | %N |
|---|---|---|---|
| Calculated | 70.00 | 6.66 | 23.34 |
| Theory | 70.16 | 6.76 | 23.42 |

EXAMPLE 8

Preparation of 4'-dimethylamino benzene-1':3 azo 1-methyl pyridinium methosulfate having the formula

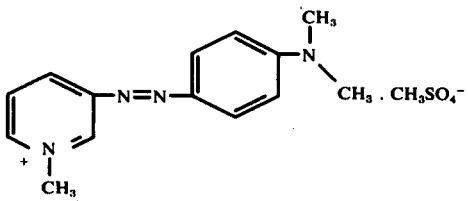

0.1 mole of the compound obtained in accordance with Example 1 is dissolved while cooling in 50cm³ of N-methyl pyrrolidone-2. To the resulting solution there added 15 g of dimethyl sulfate and the resulting mixture is left to react for 30 minutes. The above dye precipitates and is then filtered, washed with ethyl acetate and recrystallized in 60cm³ of absolute ethyl alcohol. The product melts at 202° C.

Analysis: $C_{15}H_{20}N_4O_4S$

|  | %C | %H | %N |
|---|---|---|---|
| Calculated | 51.15 | 5.68 | 15.90 |
| Found | 51.36 | 5.87 | 15.93 |

EXAMPLE 9

Preparation of 4'-bis-(2-hydroxyethyl) amino benzene-1':3 azo 1-methyl pyridinium methosulfate having the formula:

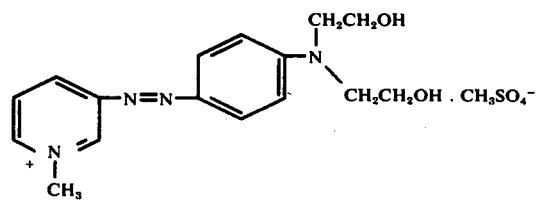

0.1 mole of the compound obtained in accordance with Example 2 is dissolved, while cooling, in 50cm³ of N-methyl pyrrolidone-2. To the resulting solution there are added 15g of dimethyl sulfate and the mixture is left to react for 30 minutes. The above dye precipitates and is then filtered, washed with ethyl acetate and recrystallized in absolute ethyl alcohol. The product melts at 134° C.

Analysis: $C_{17}H_{24}N_4O_6S \cdot 0.25H_2O$

|  | %C | %H | %N |
|---|---|---|---|
| Calculated | 49.00 | 5.89 | 13.45 |
| Found | 48.97 | 6.08 | 13.48 |

EXAMPLE 10

Preparation of 4'-amino-8'-hydroxy naphthalene-1':3 azo 1-methyl pyridinium methosulfate having the formula

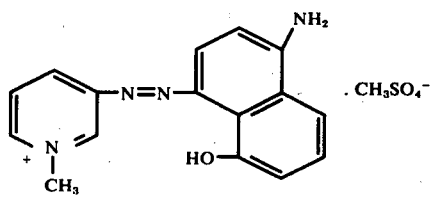

0.1 mole of the compound obtained in accordance with Example 4 is dissolved in 50cm³ of N-methyl pyrrolidone-2. To the resulting solution there are added 15g of dimethyl sulfate. The mixture is left to react for 30 minutes at which time there are added 250cm³ of ethyl acetate. The above dye which precipitates is then filtered. The product, recrystallized in 70% methanol melts, with decomposition, at 265° C.

Analysis: $C_{17}H_{18}N_4O_5S \cdot 0.25\ H_2O$

|  | %C | %H | %N |
|---|---|---|---|
| Calculated | 51.70 | 4.79 | 14.20 |
| Found | 51.74 | 5.27 | 4.27 |

EXAMPLE 11

Preparation of 4'-dimethylamino-2'-nitro benzene-1':3 azo 1-methyl pyridinium methosulfate having the formula

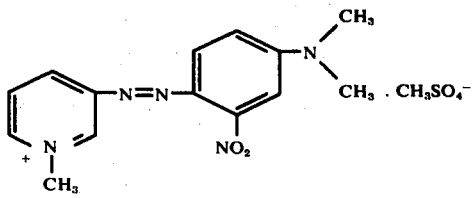

0.1 mole of the compound obtained in accordance with Example 5 is dissolved in 70cm³ of N-methyl pyrrolidone-2. To the resulting solution there are added 15g of dimethyl sulfate. The mixture is left to react for 1 hour at which time there added 250cm³ of ethyl acetate. The above dye which precipitates is then filtered. The product, recrystallized in absolute ethyl alcohol, melts at 178° C.

Analysis: $C_{15}H_{19}N_5O_6S$

|  | %C | %H | %N |
|---|---|---|---|
| Calculated | 45.35 | 4.78 | 17.62 |
| Found | 45.10 | 4.97 | 17.73 |

EXAMPLE 12

Preparation of 4'-dimethylamino-benzene-1':3 azo 1,6-dimethyl pyridinium methosulfate having the formula

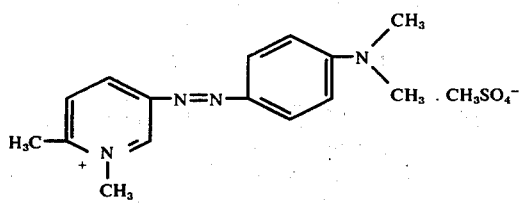

0.1 mole of the compound obtained in accordance with Example 7 is dissolved with heating in 50cm³ of N-methyl pyrrolidone-2. To the resulting solution there are added 15g of dimethyl sulfate. The mixture is agitated for 30 minutes at which time the above dye which has precipitated is filtered, washed with ethyl acetate and dried. The product, recrystallized in absolute ethyl alcohol, melts at 212° C.

Analysis: $C_{16}H_{22}N_4O_4S \cdot 0.25H_2O$

|  | %C | %H | %N |
|---|---|---|---|
| Calculated | 51.85 | 6.07 | 15.11 |
| Found | 51.67 | 5.97 | 15.19 |

EXAMPLE 13

Preparation of 4'-amino benzene-1':3 pyridine N-oxide having the formula

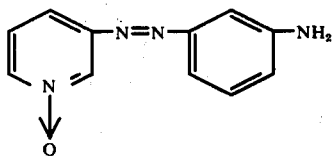

0.11 mole of the ω-salt of aniline is dissolved in 17cm³ of water. To the solution there are added 53g of crystallized sodium acetate and the mixture is cooled to +5° C. There is then slowly added a cold solution of 0.1 mole of 3-N-oxypyridyl diazonium chloride prepared according to L. Pentimalli, Tetrahedron, 9, page 194 (1960).

130g of crystallizaed sodium acetate are then added and the mixture is left to react for 1 hour. The reaction mixture is then filtered and the yellow product thus obtained is dissolved in 600cm³ of water. To this solution there are added 10cm³ of sodium lye and 10cm³ of concentrated ammonia. The resulting mixture is left to rest over night and is then heated to 50° C for 3 hours. 50g of powdered sodium chloride are added and the above dye which precipitates is filtered. The dye, recrystallized in water, melts at 245° C.

Analysis: $C_{11}H_{10}N_4O \cdot 1 H_2O$

|  | %C | %H | %N |
|---|---|---|---|
| Calculated | 56.90 | 5.17 | 24.14 |
| Found | 57.35 | 5.16 | 23.99 |

EXAMPLE 14

Preparation of 4'-dimethylamino benzene-1':3 azo pyridine N-oxide having the formula

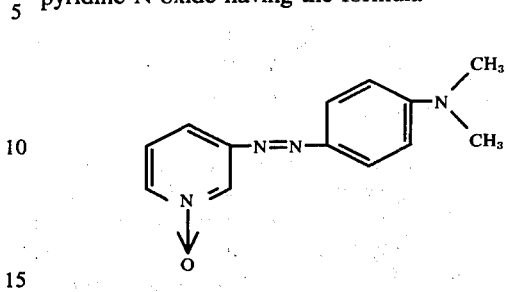

0.1 mole of N,N-dimethylaniline is dissolved in 12cm³ of acetic acid. To the resulting solution there is slowly added a cold solution of 0.1 mole of N-oxypyridyl-3 diazonium chloride prepared in accordance with the procedures disclosed by L. Pentimalli, Tetrahedron, 9 page 194, 1960. The mixture is then left to react for 15 minutes at which time there are added 50cm³ of a 40% solution of sodium acetate. The mixture is then agitated for 30 minutes at which time the above dye which has precipitated is filtered and dried. The product melts at 174° C.

EXAMPLE 15

Preparation of 4'-N,N-bis(2-hydroxyethyl) amino benzene-1':3 azo pyridine N-oxide having the formula

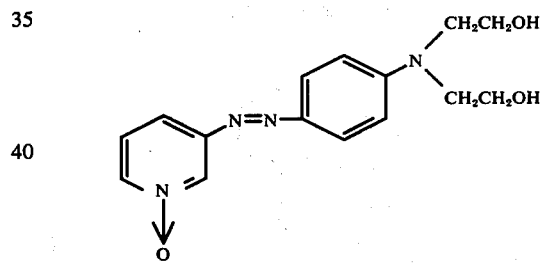

0.1 mole of N,N-bis-(2-hydroxyethyl) aniline is dissolved in 40cm³ of acetic acid. To this solution there is slowly added a cold solution of 0.1 mole of N-oxypyridyl-3 diazonium chloride, prepared as disclosed above. The mixture is left to react for 30 minutes at which time there are added 40g of crystallized sodium acetate. The above dye which has precipitated is filtered, washed with water and dried. The product, recrystallized in methanol, melts at 186° C.

Analysis: $C_{15}H_{18}N_4O_3$

|  | %C | %H | %N |
|---|---|---|---|
| Calculated | 59.61 | 5.96 | 18.54 |
| Theory | 59.38 | 5.75 | 18.80 |

EXAMPLE 16

Preparation of 4'-dimethylamino-2'-methyl benzene-1':3 azo pyridine having the formula

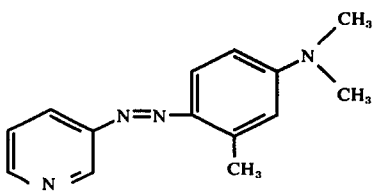

There is slowly added, with agitation and while maintaining the temperature at +5° C, a solution of 0.1 mole of the diazonium salt prepared in accordance with Example 1 to a solution of 0.1 mole of N,N-dimethyl metatoluene in 15cm³ of acetic acid. The mixture is agitated for 30 minutes at which time there are added 40g of crystallized sodium acetate. This mixture is again agitated for 15 minutes at which time the above dye which has precipitated is filtered, made into a paste in a saturated solution of sodium bicarbonate, washed with water and dried. The dye, recrystallized in cyclohexane, melts at 90° C.

Analysis: $C_{14}H_{16}N_4$

|  | %C | %H | %N |
|---|---|---|---|
| Calculated | 70.00 | 6.66 | 23.33 |
| Found | 70.18 | 6.64 | 23.20 |

EXAMPLE 17

Preparation of 4'-dimethylamino-2'-chloro benzene-1':3 azo pyridine having the formula

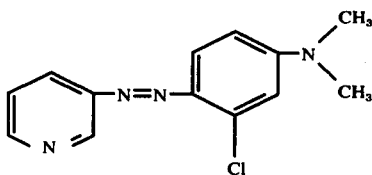

There is slowly added, while maintaining the temperature at +5° C, a solution of 0.1 mole of the diazonium salt prepared in accordance with Example 1 to a solution of 0.1 mole of N,N-dimethyl meta chloraniline in 15cm³ of acetic acid. The mixture is then agitated for 1½ hours at which time it is filtered and the dye recovered is then suspended in water and neutralized by the addition of a saturated solution of sodium bicarbonate. The neutralized dye is then filtered, worked with water and dried. The product, recrystallized in ethyl alcohol, melts at 132° C.

Analysis: $C_{13}H_{13}N_4$ Cl

|  | %C | %H | %N |
|---|---|---|---|
| Calculated | 59.90 | 4.99 | 21.50 |
| Found | 59.97 | 5.29 | 21.62 |

EXAMPLE 18

Preparation of 2', 4'-diamino-5'-methyl benzene-1':3 azo pyridine having the formula

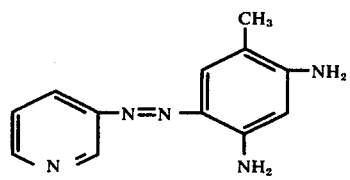

There is slowly added, while maintaining the temperature at +5° C, a solution of 0.1 mole of the diazonium salt prepared in accordance with Example 1 to a solution of 0.1 mole of 2,4-diamino toluene in 20cm³ of acetic acid. There are then added 100cm³ of water and the mixture is agitated for 30 minutes at which time the mixture is neutralized by the slow addition thereto of soda lye. Thereafter, the above dye which has precipitated is filtered, washed with water and dried. The dye, recrystallied in ethyl acetate, melts at 175° C.

Analysis: $C_{12}H_{13}N_5$

|  | %C | %H | %N |
|---|---|---|---|
| Calculated | 63.45 | 5.73 | 30.82 |
| Found | 63.59 | 5.97 | 31.04 |

EXAMPLE 19

Preparation of 2', 4'-diamino-5'-methoxy benzene-1':3 azo pyridine having the formula

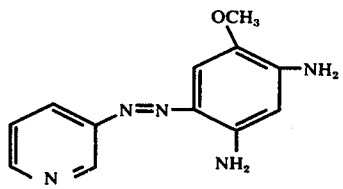

There is slowly added, while maintaining the temperature at +5° C, a solution of 0.1 mole of the diazonium salt prepared in accordance with Example 1 to a solution of 0.1 mole of 2,4-diamino anisole in 200cm³ of water. The mixture is agitated for 30 minutes at which time there are added 40g of sodium acetate to precipitate the dye. The dye is then filtered, made into a paste in a saturated solution of sodium bicarbonate, washed with water and dried. The dye, recrystallized in a 50% solution of 2-methoxy ethanol melts at 161° C.

Analysis: $C_{12}H_{13}N_5O$

|  | %C | %H | %N |
|---|---|---|---|
| Calculated | 59.25 | 5.35 | 28.80 |
| Found | 59.23 | 5.45 | 28.77 |

EXAMPLE 20

Preparation of 4'-dimethylamino-2'-methyl benzene-1':3 azo 1-ethyl pyridinium ethosulfate having the formula

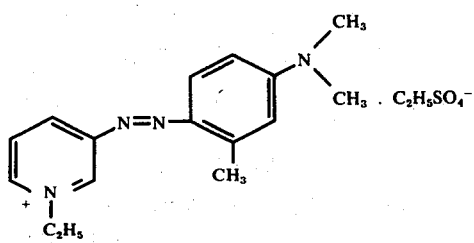

0.1 mole of the compound obtained in accordance with Example 16 is dissolved in 50cm³ of N-methyl pyrrolidone-2. To the resulting solution there are added 16g of diethyl sulfate and this mixture is heated for 1 hour. The mixture is then cooled and then there is added thereto sufficient ethyl acetate to precipitate the above dye which is then filtered, washed with ethylacetate and dried. The product, recrystallized in isopropanol, melts at 192° C.

Analysis: $C_{12}H_{26}N_4O_4S$

|  | %C | %H | %N |
|---|---|---|---|
| Calculated | 54.80 | 6.60 | 14.20 |
| Found | 54.95 | 6.78 | 14.26 |

EXAMPLE 21

Preparation of 4'-dimethylamino-2'-methyl benzene-1':3 azo 1-butyl pyridinium bromide having the formula

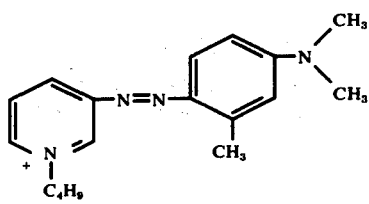

0.1 mole of the compound obtained in accordance with the procedures of Example 16 is dissolved in 50cm³ of N-methyl pyrrolidone-2. To this solution there are added 15.5g of butyl bromide. This mixture is heated for one day on a boiling water bath. It is then cooled and the above dye which has precipitated is filtered, washed with ethyl-acetate and dried. The product, recrystallized in a mixture of chloroform and ethyl acetate, melts at 182° C.

Analysis: $C_{18}H_{25}N_4Br$

|  | %C | %H | %N |
|---|---|---|---|
| Calculated | 57.30 | 6.63 | 14.85 |
| Found | 57.38 | 6.44 | 15.10 |

EXAMPLE 22

Preparation of 4'-dimethylamino-2'-chlorobenzene-1':3 azo 1-methyl pyridinium methosulfate having the formula

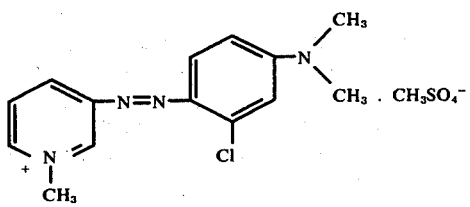

0.1 mole of the compound prepared in accordance with Example 17 is dissolved in 70cm³ of N-methyl pyrrolidone-2. To this solution there are added 14g of dimethyl sulfate. The resulting mixture is agitated for two hours at ambient temperature at which time the above dye which has precipitated is filtered, washed with ethyl acetate and dried. The product, recrystallized in ethyl alcohol, melts at 191° C.

Analysis: $C_{15}H_{19}N_4O_4S\ Cl$

|  | %C | %H | %N |
|---|---|---|---|
| Calculated | 46.55 | 4.92 | 14.48 |
| Found | 46.30 | 4.95 | 14.35 |

EXAMPLE 23

Preparation of 2', 4', -diamino-5'-methyl benzene-1':3 azo 1-methyl pyridinium methosulfate having the formula:

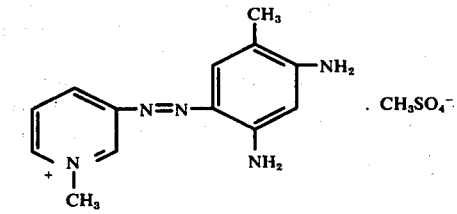

0.1 mole of the compound prepared in accordance with Example 18 is dissolved in 40cm³ of N-methyl pyrrolidone-2. To this solution there are added 14g of dimethyl sulfate and the mixture is agitated for one hour. There is then added sufficient ethyl acetate to precipitate the above dye which is then filtered and dried. The product, recrystallized in methanol, melts at 196° C.

Analysis: $C_{14}H_{19}N_5O_4S \cdot 0.5CH_3OH$

|  | %C | %H | %N |
|---|---|---|---|
| Calculated | 47.10 | 5.69 | 18.97 |
| Found | 46.99 | 5.61 | 19.15 |

EXAMPLE 24

Preparation of 4'-phenylamino benzene-1':3 azo 1-methyl pyridinium methosulfate having the formula

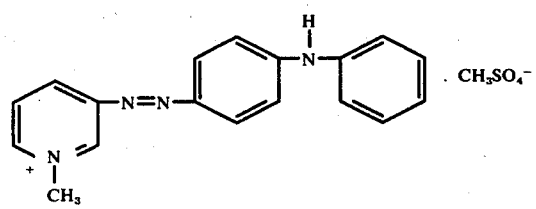

0.1 mole of the compound prepared in accordance with Example 6 is dissolved in 70cm³ of N-methyl pyrrolidone-2. To this solution there are added 14g of dimethyl sulfate and the mixture is agitated for 2 hours at ambient temperature. The above dye, which precipitates, is filtered, washed with ethyl acetate and dried. The dye, recrystallized in ethanol, melts at 189° C.

Analysis: $C_{19}H_{20}N_4O_4S$

|  | %C | %H | %N |
|---|---|---|---|
| Calculated | 57.00 | 5.00 | 14.00 |
| Found | 57.00 | 4.94 | 14.19 |

EXAMPLE 25

Preparation of 2'-acetylamino-4'-dimethylamino benzene-1':3 azo pyridine having the formula

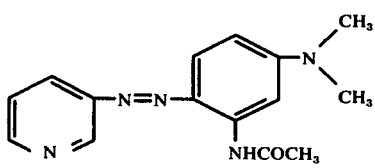

There is slowly added with agitation and while maintaining the temperature at +5° C a solution of 0.1 mole of the diazonium salt prepared in accordance with Example 1 to a solution of 0.1 mole of N,N-dimethyl meta-acetylamino aniline in 20cm³ of acetic acid. This mixture is agitated for 1 hour at which time there are then added 40g of crystallized sodium acetate. The above dye which precipitates is filtered, made into a paste in a saturated solution of sodium bicarbonate, washed with water and dried. The dye, recrystallized in ethyl acetate, melts at 124° C.

Analysis: $C_{15}H_{17}N_5O$

|  | %C | %H | %N |
|---|---|---|---|
| Calculated | 63.60 | 6.00 | 24.72 |
| Found | 63.86 | 6.02 | 24.64 |

EXAMPLE 26

Preparation of 2'-amino-4'-dimethylamino benezene-1':3 azo pyridine having the formula

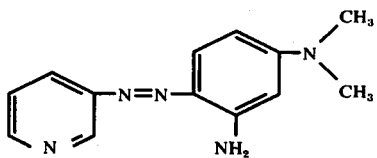

0.1 mole of the compound prepared in accordance with Example 25 is dissolved in 95cm³ of a 2.5N aqueous solution of HCl. This solution is heated at reflux for 2½ hours and is then left to cool. Thereafter, this reaction mixture is diluted with 200cm³ of water and neutralized with NaOH. The neutralized reaction mixture is then agitated for 15 minutes. The above dye which precipitates is then filtered, washed with water and dried. The dye, recrystallized in methanol, melts at 165° C.

Analysis: $C_{13}H_{15}N_5$

|  | %C | %H | %N |
|---|---|---|---|
| Calculated | 64.70 | 6.22 | 29.07 |
| Found | 64.96 | 6.05 | 28.96 |

EXAMPLE 27

Preparation of 2'-acetylamino-4'-dimethylamino benzene-1':3 azo 1-ethyl pyridinium ethosulfate having the formula

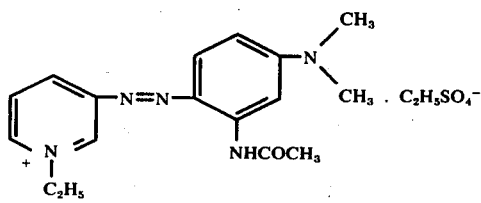

0.1 mole of the compound prepared in accordance with Example 25 is dissolved in 40cm³ of N-methyl pyrrolidone-2. To this solution there are added 16g of diethyl sulfate and the mixture is heated, with agitation, for 1 hour at 60° C. The mixture is then left to cool and the above dye, which precipitates, is then filtered, washed with ethyl acetate and dried. The dye, recrystallized in ethyl acetate, melts at 195° C.

Analysis: $C_{19}H_{27}N_5O_5S$

|  | %C | %H | %N |
|---|---|---|---|
| Calculated | 52.17 | 6.18 | 16.02 |
| Found | 52.12 | 6.30 | 15.92 |

EXAMPLE 28

Preparation of 2', 4'-diamino-5'-methoxy benzene-1':3 azo 1-methyl pyridinium methosulfate having the formula:

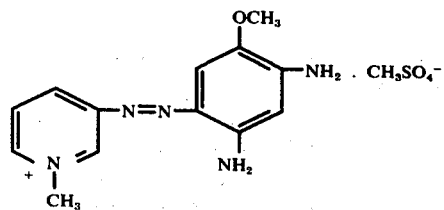

0.1 mole of the compound prepared in accordance with Example 19 is dissolved in 50cm³ of N-methyl pyrrolidone-2. To this solution there are added 14g of dimethyl sulfate and the mixture is agitated for 5 hours. There are then added 250cm³ of ethyl acetate and the mixture is again agitated for 30 minutes. The above dye, which has precipitated, is filtered, washed with ethyl acetate and dried. The dye, recrystallized in isopropanol, melts at 176° C.

Analysis: $C_{14}H_{19}N_5O_5S$

|  | %N |
|---|---|
| Calculated | 18.97 |
| Found | 19.11 |

EXAMPLE 29

Preparation of 2'-amino-4'-dimethylamino benzene-1':3 azo 1-methyl pyridinium methosulfate having the formula:

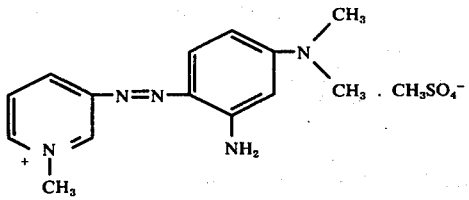

0.1 mole of the compound prepared in accordance with Example 26 is dissolved in 30cm³ of N-methyl pyrrolidone-2. To this solution there are added 17g of dimethyl sulfate. The resulting mixture is agitated for 1 hour at which time the above dye which has precipitated is filtered, washed with ethyl acetate and dried. The dye, recrystallized in methanol, melts at 237° C.

Analysis: $C_{15}H_{21}N_5O_4S$

|  | %C | %H | %N |
|---|---|---|---|
| Calculated | 49.03 | 5.73 | 19.08 |
| Found | 49.33 | 5.98 | 18.93 |

EXAMPLE 30

Preparation of 4'-dimethylamino benzene-1':3 azo 6-methoxy pyridine having the formula:

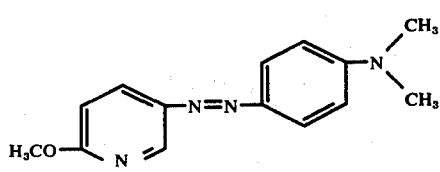

0.1 mole of 3-amino 6-methoxy pyridine is dissolved in 50cm³ of 5N HCl. The solution is then cooled to +5° C and there are dropwise added thereto 13.3cm³ of a 7.5N aqueous solution of sodium nitrite. This mixture is then agitated for 15 minutes at +5° C at which time there is added to the resulting solution 0.1 mole of N,N-dimethylaniline in 12cm³ of acetic acid. This mixture is agitated for 30 minutes at which time there are added 40g of crystallized sodium acetate to precipitate the above dye which is then filtered, washed with water and dried. The product, recrystallized in acetone, melts at 143° C.

Analysis: $C_{14}H_{16}N_4O$

|  | %C | %H | %N |
|---|---|---|---|
| Calculated | 65.65 | 6.25 | 21.85 |
| Found | 65.94 | 6.12 | 21.82 |

EXAMPLE 31

Preparation of 4'-dimethylamino benzene-1':3 azo 6-chloro pyridine having the formula:

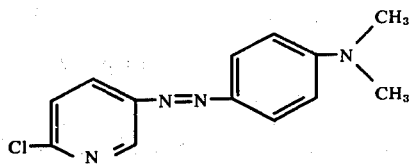

0.1 mole of 3-amino-6-chloro pyridine is dissolved in 50cm³ of 5N HCl. This solution is cooled to +5° C and there are added thereto, dropwise, 13.3cm³ of a 7.5N aqueous solution of sodium nitrite. This mixture is agitated 15 minutes at +5° C at which time there is added to the resulting solution 0.1 mole of N,N-dimethylaniline in 12cm³ of acetic acid. This mixture is agitated for 30 minutes at which time there are added 40g of crystallized sodium acetate to precipitate the above dye which is then filtered, washed with water and dried. The product, recrystallized in acetone, melts at 164° C.

Analysis: $C_{13}H_{13}N_4Cl$

|  | %C | %H | %N |
|---|---|---|---|
| Calculated | 59.90 | 4.96 | 21.50 |
| Found | 59.82 | 4.88 | 21.75 |

EXAMPLE 32

Preparation of 4'-diethylamino benzene-1':3 azo 6-butoxy pyridine having the formula:

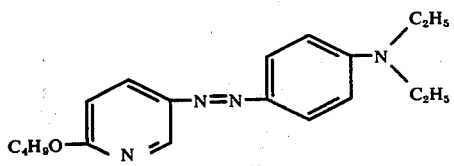

0.1 mole of 3-amino-6-butoxypyridine is dissolved in 50cm³ of 5N HCl. The solution is cooled to +5° C and there are added, dropwise, 13.3cm³ of a 7.5N aqueous solution of sodium nitrite. This mixture is agitated for 15 minutes at +5° C and there is added to the resulting solution 0.1 mole of N,N-diethylaniline in 12cm³ of acetic acid. This mixture is agitated for 30 minutes at which time there is slowly added a sufficient amount of a saturated aqueous solution of sodium carbonate to precipitate the above dye. The precipitated dye is then filtered, washed with water and dried. The product, recrystallized in ethanol, melts at 72° C.

Analysis: $C_{19}H_{26}N_4O_1$

|  | %C | %H | %N |
|---|---|---|---|
| Calculated | 70.00 | 7.97 | 17.15 |
| Found | 68.89 | 7.98 | 16.91 |

EXAMPLES OF COMPOSITIONS

Example a

A hair setting lotion composition is prepared by admixing the following components:
Dye of Example 30 —0.050g
Copolymer of vinyl acetate-crotonic acid (90/10) MW 50,000 —1.8g Copolymer of vinylacetate-vinyl-pyrrolidone (40/60) viscosity = 3.3 to 4 cps at 25° C in a 5% solution in ethanol —0.3 g
Isopropyl alcohol, q.s.p. 50° Triethanolamine, q.s.p. pH 7
Water, q.s.p. —100 cc.

This hair setting lotion when applied to bleached hair imparts thereto an esthetic, very pretty golden blond coloration.

Example b

A hair setting lotion composition is prepared by admixing the following components:
Dye of Example 1 —0.050g
Copolymer of vinyl acetate-crotonic acid as in Example a —1.8g
Copolymer of vinyl acetate-vinyl pyrrolidone, as in Example a —0.3g
Ethyl alcohol, q.s.p. 50°
Triethanolamine, q.s.p. pH 9
Water, q.s.p. 100 cc.

This hair setting lotion when applied to bleached hair imparts thereto a particularly esthetic light golden blond coloration.

EXAMPLE c

A hair setting lotion composition is prepared by admixing the following components:
Dye of Example 3 —0.050g
Copolymer of vinyl acetate-crotonic acid, as in Example a —1.8g
Copolymer of vinyl acetate-vinyl pyrrolidone, as in Example a —0.3g
Ethyl alcohol, q.s.p. 50°
Triethanolamine, q.s.p. pH 7
Water, q.s.p. —100cc.

This hair setting lotion when applied to natural blond hair imparts thereto very luminous light golden glints.

Example d

A hair setting lotion composition is prepared by admixing the following components:
Dye of Example 14 —0.050g
Copolymer of vinyl acetate-crotonic acid as in Example a —1.8g
Copolymer of vinyl acetate-vinyl pyrrolidone, as in Example a —0.3g
Ethyl alcohol, q.s.p. 50°
Triethanolamine, q.s.p. pH7
Water, q.s.p. —100cc.

This hair setting lotion when applied to hair colored a deep blond imparts thereto a very esthetic golden copper coloration.

Example e

A hair setting lotion composition is prepared by admixing the following components:
Dye of Example 14 —0.050g
Copolymer of vinyl acetate-crotonic acid, as in Example a —1.8g
Copolymer of vinyl acetate-vinyl pyrrolidone, as in Example a —0.3g
Ethyl alcohol, q.s.p. 50°
Triethanolamine, q.s.p. pH 9
Water, q.s.p. —100cc.

This hair setting lotion when applied to hair colored a light chestnut, imparts thereto a light golden copper chestnut coloration.

Example f

A hair setting lotion composition is prepared by admixing the following components:
Dye of Example 21 —0.050g
Copolymer of vinyl acetate-crotonic acid, as in Example a —1.8g
Copolymer of vinyl acetate-vinyl pyrrolidone, as in Example a —0.3g
Ethyl alcohol, q.s.p. 50°
Triethanolamine, q.s.p. pH7
Water, q.s.p. —100cc.

This hair setting lotion when applied to hair colored chestnut imparts thereto very luminous mahogany glints.

Example g

A hair setting lotion composition is prepared by admixing the following components:
Dye of Example 5 —0.050g
Copolymer vinyl acetate-crotonic acid, as in Example a —1.8g
Copolymer of vinyl acetate-vinyl pyrrolidone, as in Example a —0.3g
Ethyl alcohol, q.s.p. 50°
Citric acid, q.s.p. pH5
Water, q.s.p. —100cc.

This hair setting lotion when applied to blond hair imparts thereto particularly esthetic golden glints.

EXAMPLE h

A hair setting lotion composition is prepared by admixing the following components:
Dye of Example 14 —0.040g
Copolymer of vinyl acetate-crotonic acid as in Example a —1.8g
Ethyl alcohol, q.s.p. 55°
$H_2O_2$ (200 volumes) —5cc
Orthophosphoric acid, q.s.p. pH3
Water, q.s.p. —100cc.

This hair setting and lightening composition when applied to natural blond hair slightly lightens the hair and imparts thereto pretty, slightly golden coppery glints.

Example i a hair setting lotion composition is prepared by admixing the following components:
Dye of Example 27 —0.060g
Copolymer of vinyl acetate-crotonic acid, as in Example a —1.8g
Ethyl alcohol, q.s.p. 55°
$H_2O_2$ (200 volumes) —5cc
Orthophosphoric acid, q.s.p. pH3
Water, q.s.p. —100cc.

This hair setting lotion when applied to natural chestnut colored hair, slightly lightens the hair and imparts thereto particularly esthetic copper mahogany glints.

Example j

A hair dye composition is prepared by admixing the following components:
Dye of Example 8 —0.800g
Monoethanolamine, q.s.p. pH 6.5
Water, q.s.p. —100g.

This hair dye composition when applied to light chestnut colored hair for 20 minutes imparts thereto after rinsing and shampooing a splendid, lively, light mahogany chestnut coloration.

Example k

A hair dye composition is prepared by admixing the following components:
Dye of Example 25 — 0.250g
Hydroxyethylpropyl cellulose, sold under the name Methucel 65 Hg 4000 — 0.7g
Monoethanolamine, q.s.p. pH 10.8
Water, q.s.p. — 100g.

This hair dye composition when applied to natural deep blond hair for 15 minutes, imparts thereto, after rinsing and shampooing pretty golden glints.

Example l

A hair setting lotion composition is prepared by admixing the following components:
Dye of Example 11 — 0.030g
Copolymer of vinyl acetate-crotonic acid, as in Example a — 1.8g
Copolymer of vinyl acetate-vinyl pyrrolidone, as in Example a — 0.3g
Ethylalcohol, q.s.p. 50°
Triethanolamine, q.s.p. pH7
Water, q.s.p. — 100cc.

This hair setting lotion when applied to blond hair imparts thereto a particularly esthetic coppery blond coloration.

Example m

A hair setting lotion composition is prepared by admixing the following components:

Dye of Example 9 — 0.030g
Copoylmer of vinyl-crotonic acid, as in Example a — 1.8g
Copolymer of vinyl acetate-vinyl pyrrolidone, as in Example a — 0.3g
Ethylalcohol, q.s.p. 50°
Triethanolamine, q.s.p. pH 7
Water, q.s.p. — 100cc.

This hair setting lotion when applied to blond hair imparts thereto very luminous pink glints.

Example n

A hair setting lotion composition is prepared by admixing the following components:
Dye of Example 2 — 0.030g
Copolymer of vinyl acetate-crotonic acid, as in Example a — 1.8g
Copolymer of vinyl acetate-vinyl pyrrolidone, as in Example a — 0.3g
Ethyl alcohol, q.s.p. 50°
Triethanolamine, q.s.p. pH 7
Water, q.s.p. 100cc.

This hair setting lotion when applied to bleached hair imparts thereto a pretty golden blond coloration.

Example o

A hair setting lotion composition is prepared by admixing the following components:
Dye of Example 10 — 0.030g
Copolymer of vinyl acetate-crotonic acid, as in Example a — 1.8g
Copolymer of vinyl acetate-vinyl pyrrolidone, as in Example a — 0.3g
Ethyl alcohol, q.s.p. 50°
Triethanolamine, q.s.p. pH 7
Water, q.s.p. — 100cc.

This hair setting lotion when applied to deep blond hair imparts thereto very luminous ashen glints.

Example p

A hair setting lotion composition is prepared by admixing the following components:
Dye of Example 26 — 0.030g
Copolymer of vinyl acetate-crotonic acid, as in Example a — 1.8g
Copolymer of vinyl acetate-vinyl pyrrolidone, as in Example a — 0.3g
Ethyl alcohol, q.s.p. 50°
Triethanolamine, q.s.p. pH 7
Water, q.s.p. — 100cc.

This hair setting lotion when applied to light blond hair imparts thereto golden glints.

Example q

A hair dye composition is prepared by admixing the following components:
Dye of Example 14 — 0.020g
Paratoluylene diamine — 0.072g
Para aminophenol — 0.350g
N-methyl para aminophenol sulfate — 0.175g
Metadiamincanisole sulfate — 0.040g
Resorin — 0.040g
Meta aminophenol — 0.040g
Butyl Cellosolve — 8g
Propylene glycol — 8g
Alkylphenol polyethoxyether, sold under the name "Remcopal 334" — 22g
Alkylphenol polyethoxyether, sold under the name "Remcopal 349" — 22g
Ammonia (22°Be') — 12cc
Sodium bisulfite solution (35°Be') — 1cc
Water, q.s.p. — 100g.

To 40g of the above mixture there are added 40g of $H_2O_2$ (20 volumes). The resulting gel is then applied to light blond hair and permitted to remain in contact therewith for 30 minutes. After washing and drying the hair, there is imparted thereto a particularly luminous light coppery golden blond coloration.

Example r

A hair setting lotion composition is prepared by admixing the following components:
Dye of Example 4 — 0.006g
Copolymer of vinyl acetate-crotonic acid, as in Example a — 1.8g
Copolymer of vinyl acetate-vinyl pyrrolidone, as in Example a — 0.3g
Ethyl alcohol, q.s.p. 50°
Triethanolamine, q.s.p. pH 7
Water, q.s.p. — 100cc.

This hair setting lotion when applied to light blond hair imparts thereto very unusual pink glints.

Example s

A hair setting lotion composition is prepared by admixing the following components:
Dye of Example 23 — 0.030g
Copolymer of vinyl acetate-crotonic acid, as in Example a — 1.8g
Copolymer of vinyl acetate-vinyl pyrrolidone, as in Example a — 0.3g
Ethyl alcohol, q.s.p. 50°
Triethanolamine, q.s.p. pH 7
Water, q.s.p. — 100cc.

This hair setting lotion when applied to light chestnut colored hair imparts thereto a particularly esthetic coppery mahogany light chestnut coloration.

Example t

A hair setting lotin lotion is prepared by admixing the following components:
Dye of Example 20 — 0.050g
Copolymer of vinyl acetate-crotonic acid, as in Example a — 1.8g
Copolymer of vinyl acetate-vinyl pyrrolidone, as in Example a — 0.3g
Ethyl alcohol, q.s.p. 50°
Triethanolamine, q.s.p. pH 7
Water, q.s.p. — 100cc.

This hair setting lotion when applied to natural deep blond hair imparts thereto pretty pink glints.

Example u

A hair setting lotion composition is prepared by admixing the following components:
Dye of Example 12 — 0.050g
Copolymer vinyl acetate-crotonic acid, as in Example a — 1.8g
Copolymer of vinyl acetate-vinyl pyrrolidone, as in Example a — 0.3g
Ethyl alcohol, q.s.p. 50°
Triethanolamine, q.s.p. pH 7
Water, q.s.p. — 100cc.

This hair setting lotion when applied to light blond hair imparts thereto particularly esthetic coppery mahogany glints.

Example v

A hair setting lotion composition is prepared by admixing the following components:
Dye of Example 22 — 0.050g
Copolymer of vinyl acetate-crotonic acid, as in Example a — 1.8g
Copolymer vinyl acetate-vinyl pyrrolidone, as in Example a — 0.3g
Ethyl alcohol, q.s.p. 50°
Triethanolamine, q.s.p. pH 7
Water, q.s.p. — 100cc.

This hair setting lotion when applied to deep blond hair imparts thereto a very luminous deep pink blond coloration.

Example w

A hair setting lotion composition is prepared by admixing the following components:
Dye of Example 17 — 0.030g
Copolymer of vinyl acetate-crotonic acid, as in Example a — 1.8g
Copolymer of vinyl acetate-vinyl pyrrolidone, as in Example a — 0.3g
Ethyl alcohol, q.s.p. 50°
Triethanolamine, q.s.p. pH 7
Water, q.s.p. — 100cc.

This hair setting lotion when applied to bleached hair imparts thereto a very esthetic golden glond coloration.

Example x

A hair setting lotion composition is prepared by admixing the following components:
Dye of Example 18 — 0.030g
Copolymer of vinyl acetate-crotonic acid, as in Example a — 1.8g
Copolymer of vinyl acetate-vinyl pyrrolidone, as in Example a — 0.3g
Ethyl alcohol, q.s.p. 50°
Triethanolamine, q.s.p. pH 7
Water, q.s.p — 100cc.

This hair setting lotion when applied to blond hair imparts thereto very luminous golden glints.

Example y

A hair setting lotion composition is prepared by admixing the following components:
Dye of Example 16 — 0.050g
Copolymer of vinyl acetate-crotonic acid, as in Example a — 1.8g
Copolymer of vinyl acetate-vinyl pyrrolidone, as in Example a — 0.3g
Ethy alcohol, q.s.p. 50°
Triethanolamine, q.s.p. pH 7
Water, q.s.p. — 100cc.

This hair setting lotion when applied to natural deep blond hair imparts thereto particularly esthentic golden glints.

Example z

A hair setting lotion composition is prepared by admixing the following components:
Dye of Example 15 — 0.050g
Copolymer of vinyl acetate-crotonic acid, as in Example a — 1.8g
Copolymer of vinyl acetate-vinyl pyrrolidone, as in Example a — 0.3g
Isopropyl alcohol, q.s.p. 50°
Triethanolamine, q.s.p. pH 7
Water, q.s.p. — 100cc.

This hair setting lotion when applied to light chestnut colored hair imparts thereto very luminous coppery golden glints.

Example aa

A hair setting lotion composition is prepared by admixing the following components:
Dye of Example 7 — 0.050g
Copolymer of vinyl acetate-crotonic acid as in Example a — 1.8g
Copolymer of vinyl acetate-vinyl pyrrolidone, as in Example a — 0.3g
Ethyl alcohol, q.s.p. 50°
Triethanolamine, q.s.p. pH 7
Water, q.s.p. — 100cc.

This hair setting lotion when applied to light chestnut colored hair imparts thereto pretty golden glints.

Example ab

A hair setting lotion composition is prepared by admixing the following components:
Dye of Example 6 — 0.0055g
Copolymer of vinyl acetate-crotonic acid, as in Example a — 1.8g
Copolymer of vinyl acetate-vinyl pyrrolidone, as in Example a — 0.3g
Ethyl alcohol, q.s.p. 50°
Triethanolamine, q.s.p. pH 7
Water, q.s.p. — 100cc.

This hair setting lotion when applied to light blond hair imparts thereto pretty goldent glints.

Example ac

A hair setting lotion composition is prepared by admixing the following components:
Dye of Example 9 — 0.015g
Dye of Example 26 — 0.0075g
3-[(4'-amino)phenyl] acetylamino benzoquinoneimine — 0.010g
Copolymer of vinyl acetate-crotonic acid, as in Example a — 1.8g
Copolymer of vinyl acetate-vinyl pyrrolidone, as in Example a — 0.3g
Ethyl alcohol, q.s.p. 50°
Triethanolamine, q.s.p. pH 7
Water, q.s.p. — 100cc.

This hair setting lotion when applied to blond hair imparts thereto particularly esthetic pearly glints.

Example ad

A hair setting lotion composition is prepared by admixing the following components:
4'-dimethylamino-2'-methyl benzene-1':2 azo 5-chloro-1-methyl pyridinium methosulfate — 0.025g
4'-amino benzene-1':2 azo 1-methyl pryidinium methosulfate — 0.0125g
Dye of Example 13 — 0.0125g
Copolymer of vinyl acetate-crotonic acid, as in Example a — 1.8g
Copolymer of vinyl acetate-vinyl pyrrolidone, as in Example a — 0.3g
Ethyl alcohol, q.s.p. 50°
Triethanolamine, q.s.p. pH 7
Water, q.s.p. — 100cc.

This hair setting lotion when applied to light chestnut colored hair imparts thereto a very luminous violet light chestnut coloration.

Example ae

A hair setting lotion composition is prepared by admixing the following components:
4'-amino-8'-hydroxy naphthalene-1':2 azo 1-methyl pyridinium methosulfate — 0.025g
4'-dimethylamino benzene-1':2 azo 1-methyl pyridinium methosulfate — 0.015g
Dye of Example 14 — 0.0075g
Dye of Example 8 — 0.0025g
Copolymer of vinyl acetate-crotonic acid, as in Example a — 1.8g
Copolymer of vinyl acetate-vinyl pyrrolidone, as in Example a — 0.3g
Ethyl alcohol, q.s.p. 50°
Triethanolamine, q.s.p. pH 7
Water, q.s.p. — 100cc.

This hair setting lotion when applied to chestnut colored hair imparts thereto particularly esthetic ashen glints.

Example af

A hair setting lotion composition is prepared by admixing the following components:
4'-amino-8'-hydroxy naphthalene-1':2 azo 1-methyl pyridinium methosulfate — 0.025g
4'-dimethylamino benzene-1':2 azo 1,3-dimethyl pyridinium methosulfate — 0.0125g
Dye of Example 1 — 0.0075g
Dye of Example 14 — 0.0025g
Dye of Example 3 — 0.0025g.
Copolymer of vinyl acetate-crotonic acid, as in Example a — 1.8g
Copolymer of vinyl acetate-vinyl pyrrolidone, as in Example a — 0.3g
Ethyl alcohol, q.s.p. 50°
Triethanolamine, q.s.p. pH 7
Water, q.s.p. — 100cc.

This hair setting lotion when applied to blond hair imparts thereto a particular esthetic pearly ash blond coloration.

Example ag

A hair setting lotion composition is prepared by admixing the following components:
Dye of Example 31 — 0.010g
4'-dimethylamino benzene-1':2 azo 1,3-dimethyl pyridinium methosulfate — 0.045g
Copolymer of vinyl acetate-crotonic acid, as in Example a — 1.8g
Ethyl alcohol, q.s.p. 55°
$H_2O_2$ (200 volumes) — 5cc
Orthophosphoric acid, q.s.p. pH 3
Water, q.s.p. — 100cc.

This hair setting lotion when applied to light chestnut hair slightly lightens the hair and imparts thereto particularly esthetic violet glints.

Example ah

A hair setting lotion composition is prepared by admixing the following components:
4'-dimethylamino benzene-1':2 azo 1-methyl pyridinium methosulfate 0.030g
Dye of Example 32 0.010g
4'-amino benzene-1':2 azo 1-methyl pyridinium methosulfate 0.020g
Copolymer of vinyl acetate-crotonic acid, as in Example a 1.8g
Ethyl alcohol, q.s.p. 55° $H_2O_2$ (200 volumes 5cc
Orthophosphoric acid, q.s.p. pH 3
water, q.s.p. 100cc.

This hair setting lotion when applied to light chestnut colored hair slightly lightens the hair and imparts thereto pretty pearly pink glints.

EXAMPLE ai

A hair dye composition is prepared by admixing the following components:
4'-amino benzene 1':3 azo pyridine 0.050g
8'-hydroxy quinoline-5':2 azo 2-pyridine N-oxide 0.350g
Butyl cellosolve 8g
Propylene glycol 8g
Alkylphenol polyethoxyether, sold under the name remcopal 334 22g
Alkylphenol polyethoxyether, sold under the name Remcopal 349 22g
Ammonia (22° Be') 10cc
Water, q.s.p. 100g.

To 20g of the above mixture there are added 20g of $H_2O_2$ (20 volumes). The resulting gel is then applied to deep blond hair and is permitted to remain in contact therewith for 30 minutes. The hair is then washed and dried. The hair is lightened and exhibits a very luminous deep pinkish blond coloration.

Example aj

A hair dye composition is prepared by admixing the following components:
4'-amino benzene-1':3 azo pyridine 0.050g 8'-hydroxy quinoline-5':2 azo 2-pyridine N-oxide

| | |
|---|---|
| | 0.350g |
| Butylcellosolve | 8g |
| Propylene glycol | 8g |
| Alkylphenol polyethoxyether, sold under the name Remcopal | 22g |
| Alkylphenol polyethoxyether, sold under the name Remcopla 349 | 22g |
| Ammonia (22° Be') | 10cc |
| Water, q.s.p. | 100g. |

To 20g of the above mixture there are added 20g of water. The resulting gel is then applied to deep blond hair and is permitted to remain the contact therewith for 30 minutes. After washing and drying the hair there is imparted thereto pretty pink glints.

Example ak

A hair dye composition is prepared by admixing the following components:

| | |
|---|---|
| Dye of Example 25 | 0.015g |
| Dye of Example 4 | 0.005g |
| Paratoluylene diamine | 1.77g |
| Para aminophenol | 1.62g |
| Resorin | 1.66g |
| Metaminophenol | 0.54g |
| Butylcellosolve | 8g |
| Propylene glycol | 8g |
| Alkylphenol polyethoxyether, sold under the name Remcopal 334 | 22g |
| Alkylphenol polyethoxyether, sold under the name Remcopal 349 | 22g |
| Ammonia (22° Be') | 11cc |
| Sodium bisulfite | 1cc |
| Water, q.s.p. | 100g. |

To 40g of the above mixture there are added 40g of $H_2O_2$(20 volumes). The resulting product is then applied to deep blond hair for a period of 30 minutes, at which time, the hair is rinsed and washed. The thus treated hair exhibits a beautiful golden blond coloration.

Example al

A hair setting lotion composition is prepared by admixing the following components:

| | |
|---|---|
| Dye of Example 10 | 0.0045g |
| 4'-amino benzene-1':2 azo 1,3-dimethyl pyridinium methosulfate | 0.0125g |
| 3-N-[(4'-hydroxy-2'-chloro)phenyl]ureido-6-methyl benzoquinone imine | 0.024g |
| Copolymer of vinyl acetate-crotonic acid, as in Example a | 1.8g |
| Copolymer of vinylacetate-vinyl pyrrolidone as in Example a | 0.3g |
| Ethyl alcohol, q.s.p. 50° Triethanolamine, q.s.p. pH 7 | |
| Water, q.s.p. | 100cc. |

This hair setting lotion when applied to light chestnut colored hair imparts thereto a light pearly chestnut coloration.

What is claimed is:

1. A composition for dyeing hair comprising an aqueous or hydroalcoholic solution of (1) from 0.001 to 1 percent by weight of said composition of at least one dye compound of the formula

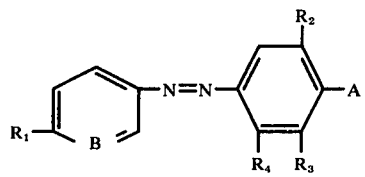

wherein B is selected from the group consisting of =N—,

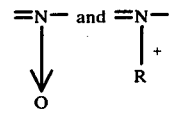

wherein R is lower alkyl containing 1–4 carbon atoms,
 $R_1$ is selected from the group consisting of hydrogen, lower alkyl containing 1–4 carbon atoms, lower alkoxy containing 1–4 carbon atoms and chlorine,
 $R_2$ is selected from the group consisting of hydrogen, methyl and methoxy,
 $R_4$ is selected from the group consisting of hydrogen, methyl, chlorine, nitro, amino and acetylamino,
 $R_3$ is hydrogen or together with $R_4$ forms an unsaturated 6-membered ring carrying a hydroxy substituent chelated with one of the nitrogen atoms of the azo link, and

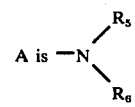

wherein $R_5$ is selected from the group consisting of hydrogen, —$CH_3$, —$C_2H_5$ and β-hydroxyethyl, and $R_6$ is selected from the group consisting of hydrogen, —$CH_3$, —$C_2H_5$, β-hydroxyethyl, phenyl and —$CH_2SO_3Na$,
 with the proviso that when B is

the anion x⁻ associated with the quaternized nitrogen atom is the anion residue of a member selected from the group consisting of organic acid and mineral acid, and
 2. an effective amount of a direct hair dye compound other than said dye compound in (1),
 said composition having a pH ranging from 3 to 11.
 said composition having a pH ranging from 3 to 11.
 2. The composition of claim 1 wherein the anion X⁻ is selected from the group consisting of methosulfate, ethosulfate, iodide, chloride and bromide.
 3. The composition of claim 1 wherein the other said direct hair dye is selected from the group consisting of azo dye, indoaniline, indophenol and indamine.
 4. A composition for dyeing hair comprising an aqueous or hydroalcoholic solution of (1) from 0.001 to 1 percent by weight of said composition of at least one dye compound of the formula

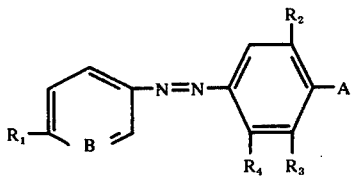

wherein B is selected from the group consisting of =N—,

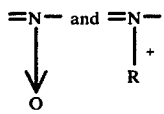

wherein R is lower alkyl containing 1–4 carbon atoms,
  $R_1$ is selected from the group consisting of hydrogen, lower alkyl containing 1–4 carbon atoms, lower alkoxy containing 1–4 carbon atoms and chlorine,
  $R_2$ is selected from the group consisting of hydrogen, methyl and methoxy,
  $R_4$ is selected from the group consisting of hydrogen, methyl, chlorine, nitro, amino and acetylamino,
  $R_3$ is hydrogen or together with $R_4$ forms an unsaturated 6-membered ring carrying a hydroxy substituent chelated with one of the nitrogen atoms of the azo link, and

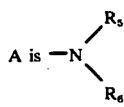

wherein $R_5$ is selected from the group consisting of hydrogen, —$CH_3$, —$C_2H_5$ and β-hydroxyethyl, and $R_6$ is selected from the group consisting of hydrogen, —$CH_3$, —$C_2H_5$, β-hydroxyethyl, phenyl and —$CH_2SO_3Na$,
  with the proviso that when B is $$=N— \atop |^+ \atop R$$

the anion $X^-$ associated with the quaternized nitrogen atom is the anion residue of a member selected from the group consisting of organic acid and mineral acid, and 2. an effective amount of an oxidation dye, said composition having a pH ranging from 3 to 11.

5. The composition of claim 4 wherein the anion $X^-$ is selected from the group consisting of methosulfate, ethosulfate, iodide, chloride and bromide.

6. A composition for dyeing hair comprising a hydroalcoholic solution of (1) from 0.001 to 1 percent by weight of said composition of at least one dye compound of the formula

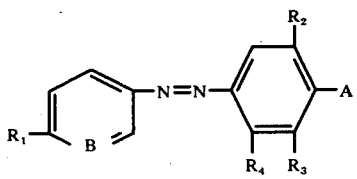

wherein B is selected from the group consisting of =N—,

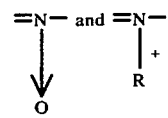

wherein R is lower alkyl containing 1–4 carbon atoms,
  $R_1$ is selected from the group consisting of hydrogen, lower alkyl containing 1–4 carbon atoms, lower alkoxy containing 1–4 carbon atoms and chlorine,
  $R_2$ is selected from the group consisting of hydrogen, methyl and methoxy,
  $R_4$ is selected from the group consisting of hydrogen, methyl, chlorine, nitro, amino and acetylamino,
  $R_3$ is hydrogen or together with $R_4$ forms an unsaturated 6-membered ring carrying a hydroxy substituent chelated with one of the nitrogen atoms of the azo link, and

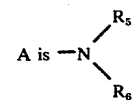

wherein $R_5$ is selected from the group consisting of hydrogen, —$CH_3$, —$C_2H_5$ and β-hydroxyethyl, and $R_6$ is selected from the group consisting of hydrogen, —$CH_3$, —$C_2H_5$, β-hydroxyethyl, phenyl and —$CH_2SO_3Na$,
  with the proviso that when B is

the anion $x^-$ associated with the quaternized nitrgen atom is the anion residue of a member selected from the group consisting of organic acid and mineral acid, and 2. 1–3 percent by weight of said composition of a cosmetic resin,
  said composition having a pH ranging from 3 to 11.

7. The composition of claim 6 wherein said hydroalcoholic solution is a solution of water and a lower alkanol present in said solution in an amount of 5 to 70 percent by weight of said composition.

8. The composition of claim 7 wherein said lower alkanol is selected from the group consisting of ethanol and isopropanol.

9. The composition of claim 7 wherein said lower alkanol is present in an amount of 20 to 70 percent by weight of said composition.

10. The composition of claim 6 wherein said cosmetic resin is selected from the group consisting of polyvinylpyrrolidone, a copolymer of crotonic acid and vinyl acetate, a copolymer of vinylpyrrolidone and vinyl acetate, a copolymer of maleic anhydride and butyl vinyl ether and the ethyl, isopropyl and butyl esters thereof and a copolymer of maleic anhydride and methyl vinyl ether and the ethyl, isopropyl and butyl esters thereof.

11. The composition of claim 6 which also includes an effective amount of an oxidizing agent.

12. A composition for dyeing hair comprising an aqueous or hydroalcoholic solution of (1) from 0.001 to 1 percent by weight of said composition of at least one dye compound of the formula

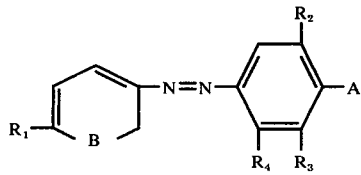

wherein B is selected from the group consisting of =N—,

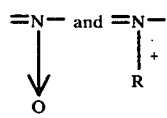

wherein R is lower alkyl containing 1–4 carbon atoms,
R$_1$ is selected from the group consisting of hydrogen, lower alkyl containing 1–4 carbon atoms, lower alkoxy containing 1–4 carbon atoms and chlorine,
R$_2$ is selected from the group consisting of hydrogen, methyl and methoxy,
R$_4$ is selected from the group consisting of hydrogen, methyl, chlorine, nitro, amino and acetylamino,
R$_3$ is hydrogen or together with R$_4$ forms an unsaturated 6-membered ring carrying a hydroxy substituent chelated with one of the nitrogen atoms of the azo link, and

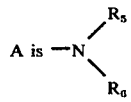

wherein R$_5$ is selected from the group consisting of hydrogen, —CH$_3$, —C$_2$H$_5$ and β-hydroxyethyl, and R$_6$ is selected from the group consisting of hydrogen, —CH$_3$, —C$_2$H$_5$, β-hydroxyethyl, phenyl and —CH$_2$SO$_3$Na,
with the proviso that when B is

the anion X⁻ associated with the quaternized nitrogen atom is the anion residue of a member selected from the group consisting of organic acid and mineral acid, and
2. an effective amount of H$_2$O$_2$ as an oxidizing agent.

13. The composition of claim 12 wherein said oxidizing agent is selected from the group consisting of H$_2$O$_2$ (200 volumes) present in an amount of 5 percent by weight of said composition and H$_2$O$_2$ (20 volumes) present in an amount of 50 percent by weight of said composition.

14. A process for dyeing human hair comprising applying an effective amount to dye said hair of a composition comprising an aqueous or hydroalcoholic solution of at least one dye compound of the formula

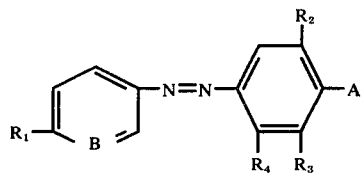

wherein B is selected from the group consisting of =N—,

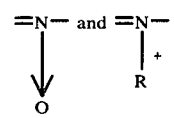

wherein R is lower alkyl containing 1–4 carbon atoms,
R$_1$ is selected from the group consisting of hydrogen, lower alkyl containing 1–4 carbon atoms, lower alkoxy containing 1–4 carbon atoms and chlorine,
R$_2$ is selected from the group consisting of hydrogen, methyl and methoxy,
R$_4$ is selected from the group consisting of hydrogen, methyl, chlorine, nitro, amino and acetylamino,
R$_3$ is hydrogen or together with R$_4$ forms an unsaturated 6-membered ring carrying a hydroxy substituent chelated with one of the nitrogen atoms of the azo link, and

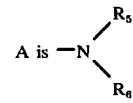

wherein R$_5$ is selected from the group consisting of hydrogen, —CH$_3$, —C$_2$H$_5$ and β-hydroxyethyl, and R$_6$ is selected from the group consisting of hydrogen, —CH$_3$, —C$_2$H$_5$, β-hydroxyethyl, phenyl and —CH$_2$SO$_3$Na,
with the proviso that when B is

the anion X⁻ associated with the quaternized nitrogen atom is the anion residue of a member selected from the group consisting of organic acid and mineral acid, said composition having a pH ranging from 3 to 11 and said compound being present in an amount ranging from 0.001 to 1 percent by weight of said composition, permitting said composition to remain in contact with said hair for a period ranging from 3 to 40 minutes, rinsing, washing and drying said hair.

15. A process for dyeing human hair comprising applying to previously washed and rinsed hair an effective amount of the composition of claim 6, rolling said hair on curlers and drying said hair.

16. A process for dyeing human hair comprising applying to previously washed and rinsed hair an effective amount of the composition of claim 11.

17. A process for dyeing human hair comprising applying an effective amount to dye said hair of the composition of claim 12, permitting said composition to remain in contact with said hair for a period ranging from 3 to 40 minutes, rinsing, washing and drying said hair.

* * * * *